US005399561A

United States Patent [19]
Chandraratna

[11] Patent Number: 5,399,561
[45] Date of Patent: Mar. 21, 1995

[54] ACETYLENES DISUBSTITUTED WITH A PHENYL OR HETEROARYL GROUP AND A 2-OXOCHROMANYL, 2-OXOTHIOCHROMANYL OR 2-OXO-1,2,3,4-TETRAHYDRO-QUINOLINYL GROUP HAVING RETINOID-LIKE BIOLOGICAL ACTIVITY

[75] Inventor: Roshantha A. Chandraratna, Mission Viejo, Calif.

[73] Assignee: Allergan, Inc., Irvine, Calif.

[21] Appl. No.: 178,714

[22] Filed: Jan. 7, 1994

Related U.S. Application Data

[60] Continuation-in-part of Ser. No. 964,227, Oct. 21, 1992, Pat. No. 5,278,318, Ser. No. 144,178, Oct. 27, 1993, Ser. No. 1,009, Jan. 6, 1993, Pat. No. 5,346,915, and Ser. No. 1,010, Jan. 6, 1993, Pat. No. 5,346,895, which is a continuation of Ser. No. 676,151, Mar. 26, 1991, abandoned, said Ser. No. 964,227, is a division of Ser. No. 749,747, Aug. 26, 1991, Pat. No. 5,162,546, which is a division of Ser. No. 549,882, Oct. 9, 1990, abandoned, which is a continuation-in-part of Ser. No. 409,488, Sep. 19, 1989, Pat. No. 4,980,369, said Ser. No. 144,178, is a division of Ser. No. 967,630, Oct. 28, 1992, Pat. No. 5,272,156, which is a division of Ser. No. 732,270, Jul. 18, 1991, Pat. No. 5,183,827, which is a division of Ser. No. 409,476, Sep. 19, 1989, Pat. No. 5,045,551, said Ser. No. 1,009, is a continuation of Ser. No. 655,524, Feb. 13, 1991, abandoned.

[51] Int. Cl.$^6$ .................. A61K 31/165; A61K 31/35; A61K 31/38; A61K 31/47
[52] U.S. Cl. .................. 514/252; 514/256; 514/312; 514/337; 514/365; 514/374; 514/432; 514/444; 514/456; 546/158; 546/269; 546/274; 544/238; 544/333; 544/405; 548/204; 548/236; 549/23; 549/60; 549/283; 549/289
[58] Field of Search ............ 546/158, 269, 274; 549/23, 60, 283, 289; 544/238, 333, 405; 548/204, 236; 514/252, 256, 312, 337, 365, 374, 432, 444, 456

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 542/429 |
| 4,391,731 | 7/1983 | Boller et al. | 252/299.62 |
| 4,695,649 | 9/1987 | Magami et al. | 560/86 |
| 4,723,028 | 2/1988 | Shudo | 560/8 |
| 4,739,098 | 4/1988 | Chandraratna | 560/3 |
| 4,740,519 | 4/1988 | Shroot et al. | 514/443 |

(List continued on next page.)

FOREIGN PATENT DOCUMENTS

| | | |
|---|---|---|
| 0130795 | 1/1985 | European Pat. Off. |
| 176034A | 4/1986 | European Pat. Off. |
| 0272921 | 6/1988 | European Pat. Off. |
| 0284288 | 9/1988 | European Pat. Off. |
| 0350846 | 7/1989 | European Pat. Off. |
| 3708060 | 9/1987 | Germany . |

(List continued on next page.)

OTHER PUBLICATIONS

A General Synthesis of Terminal and Internal Arylalkynes by the Palladium-Catalyzed Reaction of Alkynylzinc Reagents with Aryl Halides by Anthony O. King (List continued on next page.)

*Primary Examiner*—Richard L. Raymond
*Attorney, Agent, or Firm*—Gabor L. Szekeres; Robert J. Baran; Martin A. Voet

[57] ABSTRACT

Compounds of the formula

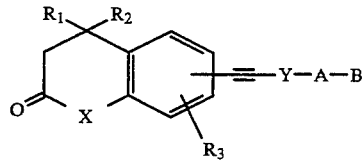

where $R_1$ and $R_2$ are hydrogen, lower alkyl of 1–6 carbons, or halogen; $R_3$ is hydrogen, lower alkyl of 1–6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$; X is O, S or NR' where R' is hydrogen or lower alkyl of 1–6 carbons; Y is phenyl or a heteroaryl group selected from a group consisting of pyridyl, thienyl, furyl, pyridazinyl, pyrimidinyl, pyrazinyl, thiazolyl and oxazolyl; A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds; B is hydrogen, COOH or a pharmaceutically acceptable salt thereof, $COOR_8$, $CONR_9R_{10}$, —CH$_2$OH, $CH_2OR_{11}$, $CH_2OCOR_{11}$, CHO, $CH(OR_{12})_2$, $CHOR_{13}O$, —$COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons, have retinoid-like biological activity.

32 Claims, No Drawings

U.S. PATENT DOCUMENTS

| | | | |
|---|---|---|---|
| 4,792,561 | 12/1988 | Walker et al. | 546/158 X |
| 4,810,804 | 3/1989 | Chandraratna | 514/311 |
| 4,826,969 | 5/1989 | Maignan et al. | 536/55.2 |
| 4,855,320 | 8/1989 | Chatterjee et al. | 514/473 |
| 4,895,868 | 1/1990 | Chandraratna | 514/432 |
| 4,927,947 | 5/1990 | Chandraratna | 549/484 |
| 4,980,369 | 12/1990 | Chandraratna | 514/432 |
| 4,992,468 | 2/1991 | Chandraratna | 514/532 |
| 5,006,550 | 4/1991 | Chandraratna | 514/456 |
| 5,013,744 | 5/1991 | Chandraratna | 514/345 |
| 5,015,658 | 5/1991 | Chandraratna | 514/432 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 514/337 |
| 5,053,523 | 10/1991 | Chandraratna | 549/398 |
| 5,068,252 | 11/1991 | Chandraratna | 514/543 |
| 5,089,509 | 2/1992 | Chandraratna | 514/337 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |
| 5,272,156 | 12/1993 | Chandraratna | 514/314 |
| 5,278,318 | 1/1994 | Chandraratna | 549/23 |

OTHER PUBLICATIONS and Ei-ichi Negishi, *J. Org. Chem.* 43 No. 2, 1978, p. 358.

Conversion of Methyl Ketones into Terminal Acetylenes and (E)-Tri-substituted Olefins of Terpenoid Origin by Ei-ichi, Anthony O. King, and William L. Klima, *J. Org. Chem.* 45 No. 12, 1980 p. 2526.

Sporn et. al. in *J. Amer. Acad. Derm.* 15:756–764 (1986).

A Convenient Synthesis of Ethynylarenes and Diethynylarenes by S. Takahashi, Y. Kuroyama, K. Sonogashira, N. Hagihara, *Synthesis* 1980 pp. 627–630.

Shudo et al. in *Chem. Phar. Bull.* 33:404–407 (1985).

Kagechika et. al. in *J. Med. Chem.* 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'-Diacyl-1,1'-biaryls. Regioncontrolled Protection of... by Mervic, et al, *J. Org. Chem.*, No. 45, pp. 4720–4725, 1980.

A Dopamine Receptor Model and Its Application in the Design of a New Class of Rigid Pyrrolo[2,3-g]isoquinoline Antipsychotics, Gary L. Olson, et al. *American Chemical Society*, 1981, vo. 24, No. 9, pp. 1026–1031.

6.2.3 Conformational Restriction, Williams, et al., *Drug Discovery and Development*, 1987 The Humana Press, pp. 54–55.

V. Retinoid Structure–Biological Activity Relationships, Chemistry and Biology of Synthetic Retinoids, pp. 324–356 Davis et al. *J. Organomettalic Chem* 387 (1990) 381–390.

*Effects of 13–Cis–Retinoic Acid, All–Trans–Retinoic Acid, and Acitretin on the Proliferation, Lipid Synthesis and Keratin Expression of Cultured Human Sebocytes In Vitro*, C. C. Zouboulis, The Journal of Investigative Dermatology, vol. 96, No. 5, May 1991, pp. 792–797.

Organ maintenance of human sebaceous glands: in vitro effects of 13–cis retinoic acid and testosterone, John Ridden, et al., *Journal of Cell Science*, Vo. 95, 1990, pp. 125–136.

Characterization of Human Sebaceous Cells In Vitro, Thomas I. Doran, et al., *The Journal of Investigative Dermatology*, vol. 96, No. 3, Mar., 1991.

Davies et al, J. Organometallic Chem., vol. 387 (1990) pp. 381–390.

ACETYLENES DISUBSTITUTED WITH A PHENYL OR HETEROARYL GROUP AND A 2-OXOCHROMANYL, 2-OXOTHIOCHROMANYL OR 2-OXO-1,2,3,4-TETRAHYDRO-QUINOLINYL GROUP HAVING RETINOID-LIKE BIOLOGICAL ACTIVITY

CROSS-REFERENCE TO RELATED APPLICATIONS

The present invention is a continuation-in-part of pending application Ser. No. 07/964,227, filed on Oct. 21, 1992, now U.S. Pat. No. 5,278,318, which is a divisional of application Ser. No. 07/749,747, filed on Aug. 26, 1991, now U.S. Pat. No. 5,162,546, which is a divisional of application Ser. No. 07/549,882, filed on Oct. 9, 1990, now abandoned, which is a continuation-in-part of application Ser. No. 07/409,488, on Sep. 19, 1989, now U.S. Pat. No. 4,980,369; a continuation-in-part of pending application Ser. No. 08/144,178, filed on Oct. 27, 1993, which is a divisional of application Ser. No. 07/967,630, filed on Oct. 28, 1992, now U.S. Pat. No. 5,272,156, which is a divisional of application Ser. No. 07/732,270, filed on Jul. 18, 1991, now U.S. Pat. No. 5,183,827, which is a divisional of application Ser. No. 07/409,476, filed on Sep. 19, 1989, now U.S. Pat. No. 5,045,551; a continuation-in-part of pending application Ser. No. 08/001,009, filed on Jan. 6, 1993, now U.S. Pat. No. 5,346,915, which is a continuation of application Ser. No. 07/655,524, filed on Feb. 13, 1991, now abandoned; and a continuation-in-part of pending application Ser. No. 08/001,010, filed on Jan. 6, 1993, U.S. Pat. No. 5,346,895, which is a continuation of application Ser. No. 07/676,151, filed on Mar. 26, 1991, now abandoned.

BACKGROUND OF THE INVENTION

1. Field of the Invention

The present invention is directed to novel compounds which have retinoid-like biological activity. More specifically, the present invention relates to ethyne compounds which have a phenyl or a heteroaryl substituent and also a 2-oxochromanyl, 2-oxothiochromanyl or 2-oxo-1,2,3,4-tetrahydroquinolinyl substituent. The phenyl or heteroaryl group may have an acid or ester function, which may also be converted to an alcohol, aldehyde or ketone, or derivatives thereof, or may be reduced to $-CH_3$.

2. Related Art

Compounds which have retinoid like activity are well known in the art, and are described in numerous United States and foreign patents and in scientific publications. It is generally known and accepted in the art that retinoid like activity is useful for treating animals of the mammalian species, including humans, for curing or alleviating the symptoms and conditions of numerous diseases and conditions. In other words, it is generally accepted in the art that pharmaceutical compositions having a retinoid like compound or compounds as the active ingredient are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus) for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

U.S. Pat. No. 4,810,804 discloses such disubstituted acetylene compounds wherein one of the substituents of the acetylene group is a substituted phenyl group, and the second substituent is substitited or unsubstituted 6-chromanyl, 6-thiochromanyl or 6-tetrahydroquinolinyl group. The compounds disclosed and claimed in U.S. Pat. No. 4,810,804 have retinoid acid-like biological activity.

A published European patent application of the present applicant (Publication No. 0284288, published on Sep. 28, 1988) describes compounds having retinoic acid-like activity which are 4,4-disubsituted 6-chromanyl, 4,4-disubsituted 6-thiochromanyl and 4,4-disubsituted 6-tetrahydroquinolinyl acetylenes also subsitituted by a substituted heteroaryl group.

U.S. Pat. Nos. 5,013,744, 5,023,341, 5,053,523, and 5,089,509 describe ethyne compounds substituted with a heteroaromatic or monocyclic aromatic substituent and also with a second monocyclic aromatic or heteroaromatic substituent. The compounds described in these patents have retinoid-like biological activity.

SUMMARY OF INVENTION

The present invention relates to compounds of Formula 1

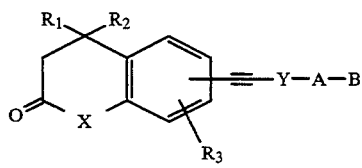

Formula 1 where $R_1$ and $R_2$ are hydrogen, lower alkyl of 1-6 carbons, or halogen;

$R_3$ is hydrogen, lower alkyl of 1-6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$;

X is O, S or NR' where R' is hydrogen or lower alkyl of 1-6 carbons;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0-5, lower branched chain alkyl having 3-6 carbons, cycloalkyl having 3-6 carbons, alkenyl having 2-6 carbons and 1 or 2 double bonds, alkynyl having 2-6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5-10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2-5 carbons.

In a second aspect, this invention relates to the use of the compounds of Formula 1 as regulators for cell proliferation and differentiation, and particularly as agents for treating dermatoses, such as acne, Darier's disease, psoriasis, icthyosis, eczema, atopic dermatitis, and for treating and preventing malignant hyperproliferative diseases such as epithelial cancer, breast cancer, prostatic cancer, head and neck cancer and myeloid leukemias, for reversing and preventing artherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and in reversing and preventing the effects of sun damage to skin.

This invention also relates to a pharmaceutical composition comprising a compound of Formula 1 in admixture with a pharmaceutically acceptable excipient.

In another aspect, this invention relates to the process for making a compound of Formula 1, which process comprises reacting a compound of Formula 2 with a compound of Formula 3 in the presence of cuprous iodide and Pd(PQ$_3$)$_2$Cl$_2$ (Q is phenyl) or a similar complex.

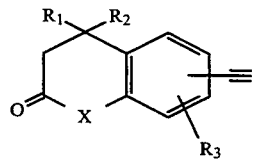

Formula 2

X'—Y—A—B    Formula 3 where X, Y, R$_1$, R$_2$ and R$_3$ are as described above, X' is a halogen, preferably I; A is the same as defined above; and B is H, or a protected acid, alcohol, aldehyde, or ketone, giving the corresponding compound of Formula 1; or to the process of making a compound of Formula 1 which consists of reacting a zinc salt of Formula 4 with a compound of Formula 3 in the presence of Pd(PQ$_3$)$_4$ (Q is phenyl) or a similar complex.

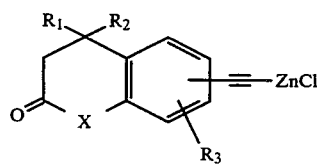

Formula 4 where X, R$_1$, R$_2$ and R$_3$ are the same as defined above, giving the corresponding compound of Formula 1; or homologating a compound of Formula 5

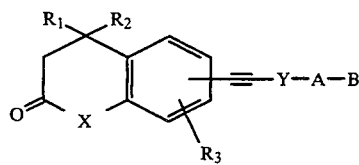

Formula 5 where A is (CH$_2$)$_n$ and n is 0-4 to give an acid of Formula 1; or
converting an acid of Formula 1 to a salt; or
forming an acid addition salt;
converting an acid of Formula 1 to an ester; or
converting an acid of Formula 1 to an amide; or
reducing an acid of Formula 1 to an alcohol or akdehyde; or
converting an alcohol of Formula 1 to an ether or ester; or
oxidizing an alcohol of Formula 1 to an aldehyde; or
converting an aldehyde of Formula 1 to an acetal; or
converting a ketone of Formula 1 to a ketal.

DETAILED DESCRIPTION OF THE INVENTION

General Embodiments

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cycloalkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. It includes organic and inorganic esters. Where B (of Formula 1) is —COOH, this term covers the products derived from treatment of this function with alcohols or thioalcohols preferably with aliphatic alcohols having 1-6 carbons. Where the ester is derived from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is defined as above.

The term "amides" has the meaning classically accorded that term in organic chemistry. In this instance it includes the unsubstituted amides and all aliphatic and aromatic mono- and di- substituted amides.

A pharmaceutically acceptable salt may be prepared for any compounds in this invention having a functionality capable of forming such salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

The compounds of the present invention may contain one or more double bonds, and therefore may have trans and cis (E and Z) isomers. In adddition, the compounds of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With reference now to Formula 1, the preferred compounds of this invention are those where X is O or S (chroman and thiochroman derivatives), with the chromans (X is O) being particularly preferred.

With reference to the group Y in Formula 1, compounds are preferred where Y is phenyl, pyridyl, thienyl or furyl, with the phenyl and pyridiyl derivatives being particularly preferred. When Y is phenyl compounds are preferred where the ethynyl group and the A-B group are attached to the 1 and 4 positions respectively of a benzene ring (i.e., where the phenyl moiety of the compound is para substituted). When the Y group is pyridyl or thienyl, compounds are preferred where the ethynyl group and the A-B group are attached to the 2 and 5 positions respectively of a pyridine ring (the 6 and 3 positions of the nicotinic acid nomenclature being equivalent to the 2/5 designation in the pyridine nomenclature) or to the 5 and 2 positions respectively of a thiophene group, respectively.

With regard to the A-B side chain (substituent) on the phenyl or heteroaryl group Y, compounds are preferred where A is $(CH_2)_n$ and n is 0. With regard to group B, compounds are preferred where and B is —COOH, an alkali metal salt or organic amine salt, or a lower alkyl ester therof. The most preferred compounds of the invention are shown in Formula 6:
 Ethyl 6-[4,4-dimethyl-2-oxo-6-chromanyl]-ethynylnicotinate (Compound 1, $X''$=N, $R_8$=$C_2H_5$);
 Ethyl 4-[4,4-dimethyl-2-oxo-6-chromanyl]-ethynylbenzoate (Compound 2, $X''$=CH, $R_8$=$C_2H_5$), and
 4-[4,4-dimethyl-2-oxo-6-chromanyl]-ethynyl-benzoic acid (Compound 2a, $X''$=CH, $R_8$=H).

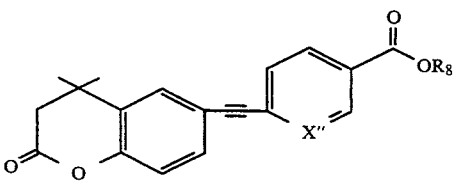

Formula 6

The compounds of this invention may be administered systemically or topically, depending on such considerations as the condition to be treated, need for site-specific treatment, quantity of drug to be administered, and numerous other considerations.

In the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, Remington's Pharmaceutical Science, Edition 17, Mack Publishing Company, Easton, Penn. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoid-like compounds will be effected by administration of the therapeutically effective dose of one or more compounds of the instant invention. A therapeutic concentration will be that concentration which effects reduction of the particular condition, or retards it expansion. In certain instances, the compound potentially may be used in prophylactic manner to prevent onset of a particular condition. A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg per day of body weight would be expected to effect a therapeutic result in the treatment of many disease for which these compounds are useful.

The retinoid-like activity of these compounds is confirmed through the classic measure of retinoic acid activity involving the effects of retinoic acid on ornithine decarboxylase. The original work on the correlation between retinoic acid and decrease in cell proliferation was done by Verma & Boutwell, Cancer Research, 1977, 37,2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Res: 1662–1670,1975 may be used to demonstrate inhibition of TPA induction of ODC by compounds of this invention. The results of this assay for certain examplary compounds of the invention are shown in Table 1 below, wherein the percentage of ODC inhibition attained by 30, 100 and 1,000 nanomolar (nmol) concentration of the respective compound is indicated.

TABLE 1

| Compound # | % inhibition | | |
|---|---|---|---|
| | 30 nmol | 100 nmol | 1,000 nmol |
| 1 | 55% | 63% | |
| 2 | 80% | 81% | |
| 2a | 64% | — | 78% |

SPECIFIC EMBODIMENTS

Synthetic Processes for Preparing Compounds of the Invention

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Compounds of Formula 1 where X is O (chroman derivatives) are prepared as per Reaction Schemes 1 and 2.

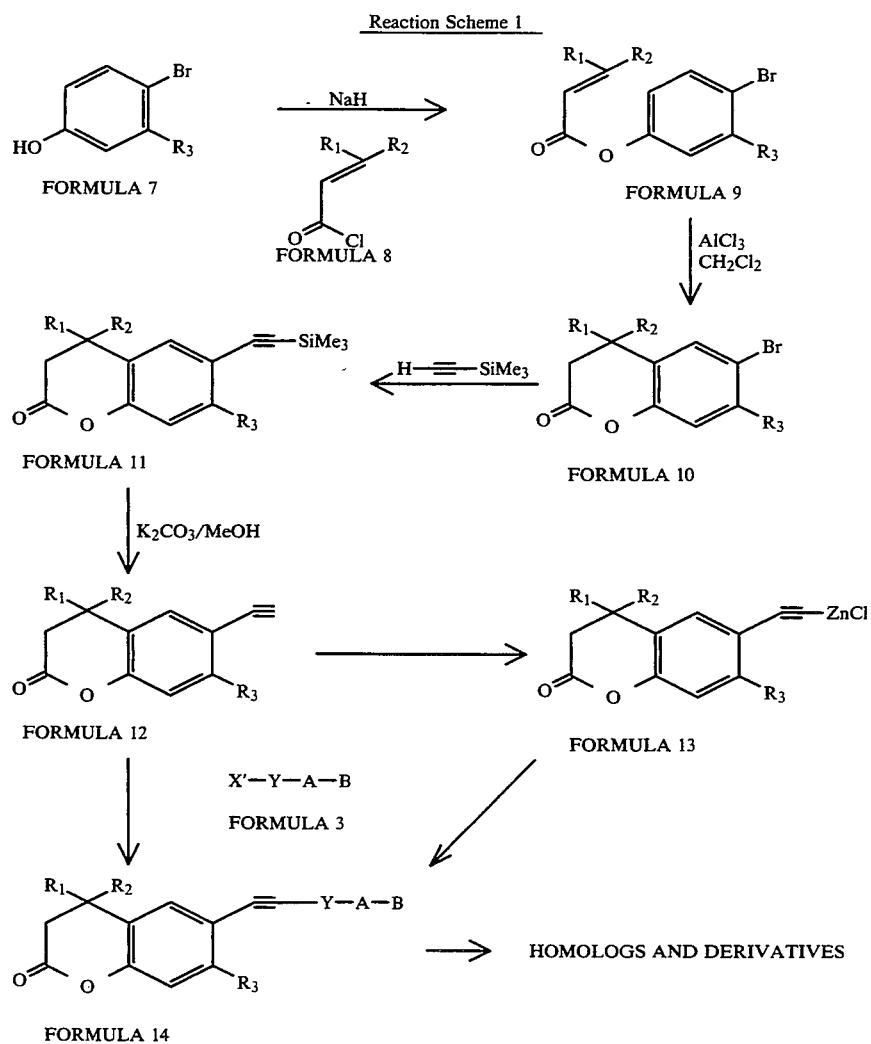

Reaction Scheme 1

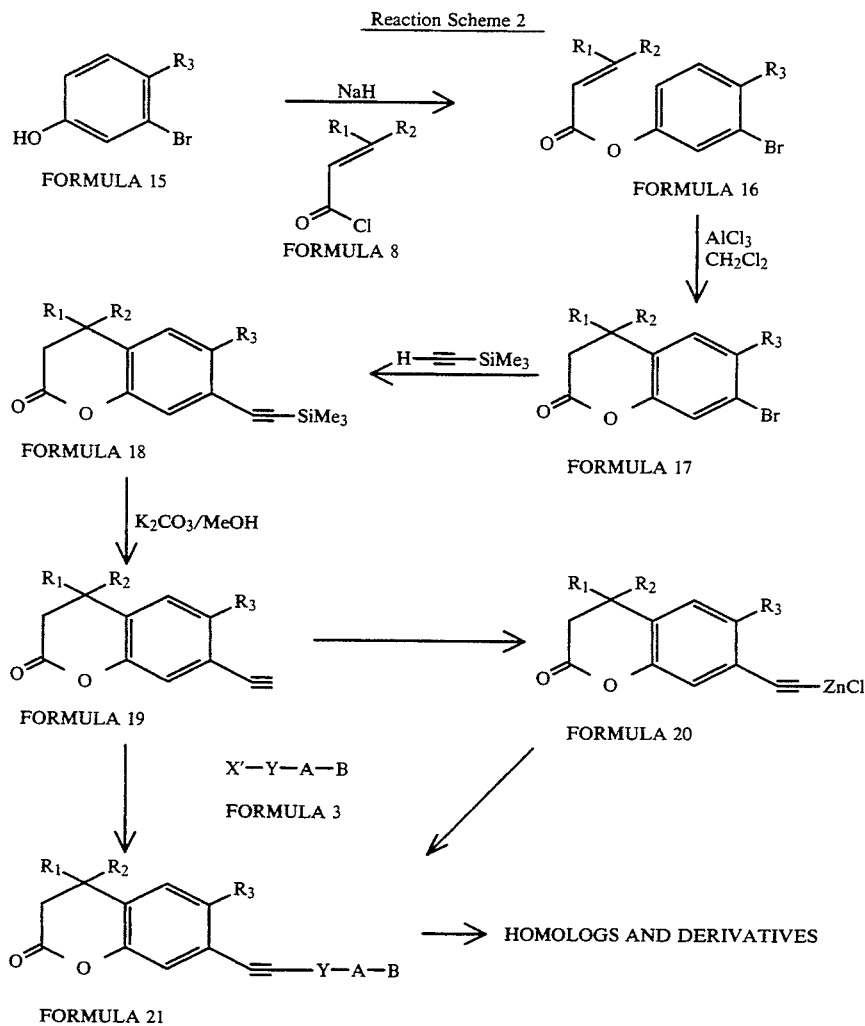

Reaction Scheme 2

In Reaction Schemes 1 and 2 $R_1$-$R_3$ are defined as in connection with Formula 1, and X', Y, A and B are defined as in connection with Formula 3. As it will become apparent from the schemes, in Reaction Scheme 1 the ethynyl group is located in the 6-position of the chroman ring, whereas in Reaction Scheme 2 the ethynyl group is located in the 7-position of the chroman ring. A general description of the synthetic steps outlined in Reaction Schemes 1 and 2 is as follows.

In Reaction Scheme 1 4-bromophenol (Formula 7), or a 4-bromophenol substituted in the 3-(meta) position by an alkyl substituent ($R_3$ in Formula 7) is acylated with an acylating agent, such as an acid chloride (Formula 8) derived from an appropriately substituted acrylic acid. Thus, the $R_1$ and $R_2$ substitutents of the target compound are introduced through this acrylic acid derivative (Formula 8). The acylation with the acid chloride (Formula 8) is preferably conducted in the presence of a strong base (e.g., sodium hydride) in an inert solvent (such as tetrahydrofuran). The resulting substituted phenyl acrylate is shown in Reaction Scheme 1 as Formula 9. The substituted phenyl-acrylate (Formula 9) is ring closed under Friedel-Crafts type reaction conditions (AlCl₃ catalyst, in an inert solvent, such as methylene chloride) to provide the 2-oxo-6-bromo-chroman (Formula 10) which bears, in the 4-position, the $R_1$ and $R_2$ substituents and in the 7 positions the $R_3$ substituent (as applicable). To introduce the acetylene (ethyne) portion into the molecule, the substituted 6-bromo-2-oxo-chroman (Formula 10) is reacted with trimethylsityl acetylene in the presence of cuprous iodide and a suitable catalyst, typically having the formula Pd(PQ₃)₂Cl₂ (Q is phenyl). The reaction is typically conducted in the presence of a bis(triphenylphosphine) palladium (II) chloride catalyst and an acid acceptor (such as triethylamine) under an inert gas (argon) atmosphere, by heating in a sealed tube. The resulting 6-trimethylsilylethynyl-2-oxo-chroman is shown as Formula 11 in Reaction Scheme 1.

As shown in Reaction Scheme 1, the trimethylsilyl moiety is removed from the 6-trimethylsilylethynyl-2-oxo-chroman (Formula 11) in the next synthetic step, to provide the ring substituted 6-ethynyl-2-oxo-chroman derivative (Formula 12). The latter reaction is conducted under basic conditions, preferably under an inert gas atmosphere.

In order to introduce a phenyl or heteroaryl substitutent on the acetylene (ethyne) portion of a compound of Formula 12, the latter compound is coupled with the reagent X'-Y-A-B (Formula 3). In other words, the phenyl or heteroaryl substitutent is introduced into the 6-ethynyl-2-oxo-chroman (Formula 12) by reacting the latter with a halogen substituted phenyl or heteroaromatic compound of Formula 3 in which the phenyl or heteroaromatic nucleus (Y) either has the desired substituent [A-B] or wherein the actual subsituent A-B can be readily converted to the desired substituent by means of organic reactions well known in the art.

Coupling of the 6-ethynyl-2-oxo-chroman (Formula 12) with the reagent X'-Y-A-B is affected directly in the presence of cuprous iodide, a suitable catalyst, typically of the formula Pd(PQ$_3$)$_2$Cl$_2$ and an acid acceptor, such as triethylamine, by heating in a sealed tube under an inert gas (argon) atmosphere. Alternatively, a metal salt, such as the zinc salt of Formula 13 derived from the ethynyl compound of Formula 12 is reacted with the reagent of Formula 3 in the presence of a palladium complex catalyst having the formula Pd(PQ$_3$)$_4$ (Q is phenyl) or similar complex.

The resulting disubstituted acetylene compound (Formula 14) may be the target compound made in accordance with the invention, or may be readily converted into the target compound by such steps as salt formation, esterification, deesterification, homologation, amide formation and the like. These steps are further discussed below.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and Protecting Groups, Ed. Greene, John Wiley & Sons, 1981.

A means for making compounds where A is (CH$_2$)$_n$ (n is 1-5) is to subject the compounds of Formula 1, where B is an acid or other function, to homologation, using the well known Arndt-Eistert method of homologation, or other known homologation procedures.

Compounds of Formula 1, where A is an alkenyl group having one or more double bonds can be made for example, by having the requisite number of double bonds incorporated into the halogenated bicyclic aryl or bicyclic heteroaryl intermediate which is reacted with the ethyne compound or its metal salt, as shown in Reaction Scheme 1. Generally speaking, such compounds where A is an unsaturated carbon chain can be obtained by synthetic schemes well known to the practicing organic chemist; for example by Wittig and like reactions, or by introduction of a double bond by elimination of halogen from an alpha-halo-carboxylic acid, ester or like carboxaldehyde. Compounds of Formula 1 where the A group has a triple (acetylenic) bond can be made by using the corresponding aryl or heteroaryl aldehyde intermediate. Such intermediate can be obtained by reactions well known in the art, for example, by reaction of a corresponding methyl ketone with strong base, such as lithium diisopropyl amide.

The acids and salts derived from compounds of Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1-4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1-4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds of Formula 1 where B is H can be prepared from the corresponding halogenated aromatic compounds, preferably where the halogen is I.

Referring now to Reaction Scheme 2, 3-bromophenol (Formula 15), or a 3-bromophenol substituted in the 4-(para) positions by by an alkyl substituent (R$_3$ in Formula 15) is acylated with an acylating agent, such as an acid chloride (Formula 8) derived from an appropriately substituted acrylic acid. In Reaction Scheme 2, just as in Reaction Scheme 1, the R$_1$ and R$_2$ substitutents of the target compound are introduced through this acrylic acid derivative (Formula 8). The acylation with the acid chloride (Formula 8) is preferably conducted in the presence of a strong base (e.g., sodium hydride) in an inert solvent (such as tetrahydrofuran). The resulting substituted phenyl acrylate compound is shown in Reaction Scheme 2 as Formula 16. The substituted phenylacrylate (Formula 16) is ring closed under Friedel-Crafts type reaction conditions ($AlCl_3$ catalyst, in an inert solvent, such as methylene chloride) to provide the 2-oxo-7-bromo-chroman (Formula 17) which bears, in the 4-position, the $R_1$ and $R_2$ substituents and in the 6 position the $R_3$ substituent (as applicable). To introduce the acetylene (ethyne) portion into the molecule, the substituted 7-bromo-2-oxo-chroman (Formula 17) is reacted with trimethylsilyl acetylene in the presence of cuprous iodide and a suitable catalyst, typically having the formula $Pd(PQ_3)_2Cl_2$ (Q is phenyl), as defined in Reaction Scheme 1. The resulting 7-trimethylsilyl-ethynyl-2-oxo-chroman is shown as Formula 18 in Reaction Scheme 2.

In Reaction Scheme 2, just as in Reaction Scheme 1, the trimethylsilyl moiety is removed from the 7-trimethylsilylethynyl-2-oxo-chroman (Formula 18) under basic conditions, to provide the ring substituted 7-ethynyl-2-oxo-chroman derivative (Formula 19).

The 7-ethynyl-2-oxo-chroman derivative of Formula 19 may be converted into the target compounds of the invention in synthetic steps which are analogous to the conversion of 6-ethynyl-2-oxo-chromans (Formula 12) into the corresponding target 2-oxo-chroman derivatives (See Reaction Scheme 1). Briefly, a compound of Formula 19 is preferably heated with a reagent X'-Y-A-B (Formula 3) in the presence of cuprous iodide, a suitable catalysts, typically of the formula $Pd(PQ_3)_2Cl_2$ and an acid acceptor, such as triethylamine, by heating in a sealed tube under an inert gas (argon) atmosphere. This coupling reaction, yields the target chroman compounds of Formula 21 or such derivatives which are readily converted into the target compounds by protection, deprotection, esterification, deesterification, homologation and the like, as is discussed in connection with Reaction Scheme 1.

Alternatively, the 7-ethynyl-2-oxo-chroman compounds of Formula 19 may first be converted to the corresponding metal (zinc) salt of Formula 20 and thereafter coupled with the reagent X'-Y-A-B (Formula 3) under conditions which are similar to the conditions described in Reaction Scheme 1 for coupling of compounds of Formula 13 with the same reagent.

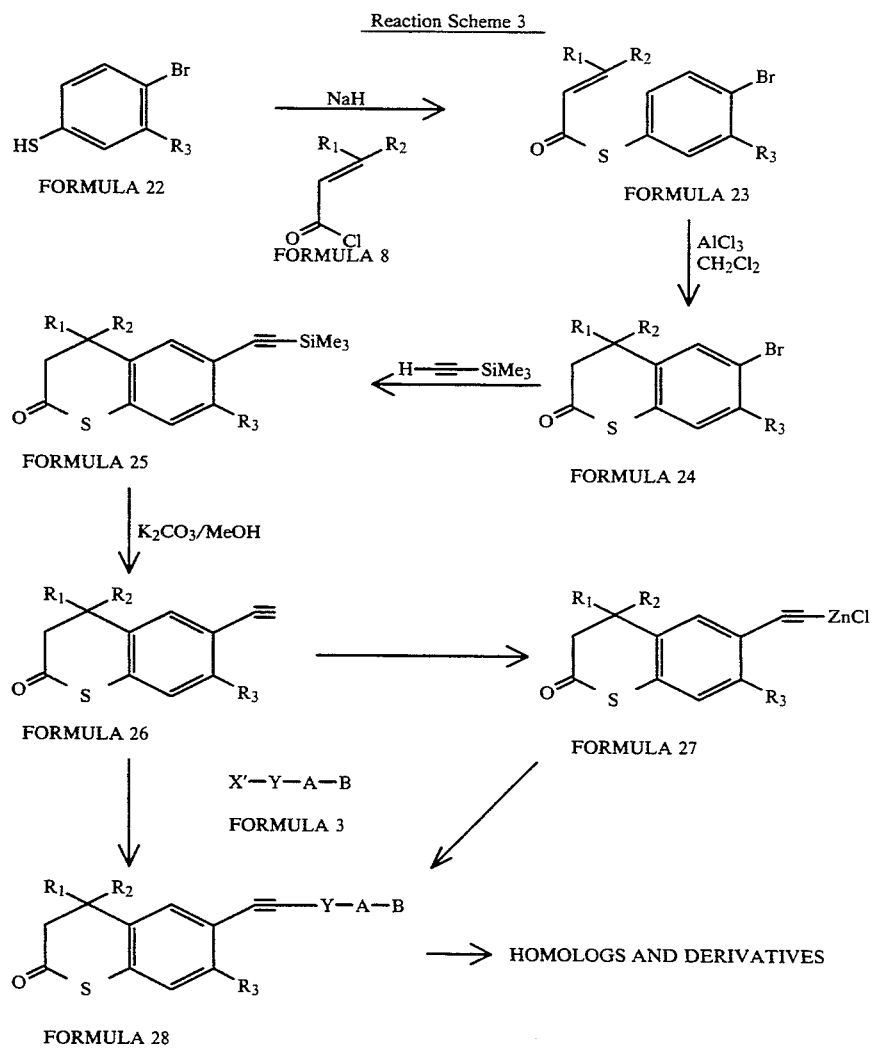

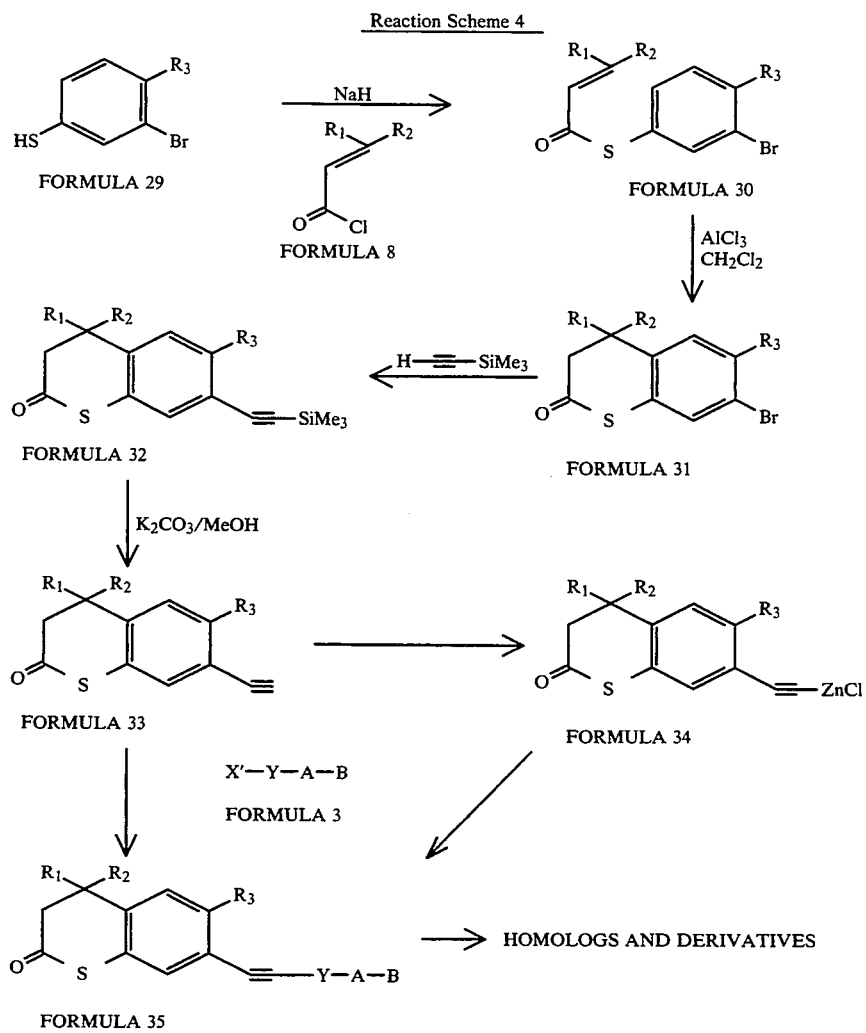

Reaction Scheme 4

Compounds of Formula 1 where X is S are prepared as per Reaction Scheme 3 and 4.

In Reaction Schemes 3 and 4 the definitions of $R_1$–$R_3$, Y, A, B, and X' are the same as in Reaction Schemes 1 and 2. In Reaction Scheme 3 the ethynyl group is located in the 6 position of the thiochroman ring. In Reaction Scheme 4 the ethynyl group is located in the 7 position of the thiochroman ring. Many of the synthetic steps are analogous to the steps described above in connection with Reaction Schemes 1 and 2, and these steps are not described in detail again.

Thus, in Reaction Scheme 3 4-bromo-thiophenol (Formula 22), or a 4-bromo-thiophenol substituted in the 3-(meta) position by an alkyl substituent ($R_3$) is acylated with the acylating agent of Formula 8. The resulting substituted thioester (Formula 23) which contains the olefinic bond of the acrylic acid moiety is ring closed in the presence of a Friedel-Crafts type catalysts, as in the preceding reaction schemes. To introduce the acetylene (ethyne) portion into the molecule, the substituted 2-oxo-6-bromo-thiochroman (Formula 24) is reacted with trimethylsilyl acetylene as in the preceding reaction schemes to give 6-trimethylsilylethynyl-2-oxo-thiochroman (Formula 25). The trimethylsilyl moiety is removed from the 6-trimethylsilylethynyl-2-oxo-thiochroman (Formula 25) in the next synthetic step, to provide the ring substituted 6-ethynyl-2-oxo-thiochroman derivative (Formula 26).

The compound of Formula 26 is then coupled with the reagent X'-Y-A-B (Formula 3) either directly (in the presence of cuprous iodide, and a suitable catalyst, typically of the formula Pd($PQ_3$)$Cl_2$, and an acid acceptor, such as triethylamine) or as its metal (zinc) salt Formula 27 to yield the compound of Formula 28, as described in the preceding reaction schemes.

In accordance with Reaction Scheme 4, 3-bromo-thiophenol, or a 3-bromo-thiophenol substituted in the 4-(para) positions by an alkyl substituent ($R_3$) is acylated with the acylating agent of Formula 8 to yield the substituted thioester compound of Formula 30. The substituted thioester (Formula 30) is ring closed under Friedel-Crafts type reaction conditions, as in the preceding reaction schemes, to provide the 2-oxo-7-bromo-thiochroman (Formula 31). The substituted 7-bromo-2-oxo-thiochroman (Formula 31) is reacted with trimethylsilyl acetylene, as described above, to yield 7-trimethylsilylethynyl-2-oxo-thiochroman (Formula 32). The trimethylsilyl moiety is removed from the 7-trimethylsilylethynyl-2-oxo-thiochroman (Formula 32) under basic conditions, to provide the ring substituted 7-ethynyl-2-oxo-thiochroman derivative (Formula 33) which is coupled with the reagent X'-Y-A-B (Formula 3) either directly, or in the form of a metal (zinc) salt (Formula 34). This coupling reaction, yields the target 2-oxo-thiochroman compounds of Formula 35 or such derivatives which are readily converted into the target compounds, as described above.
Reaction Scheme 5
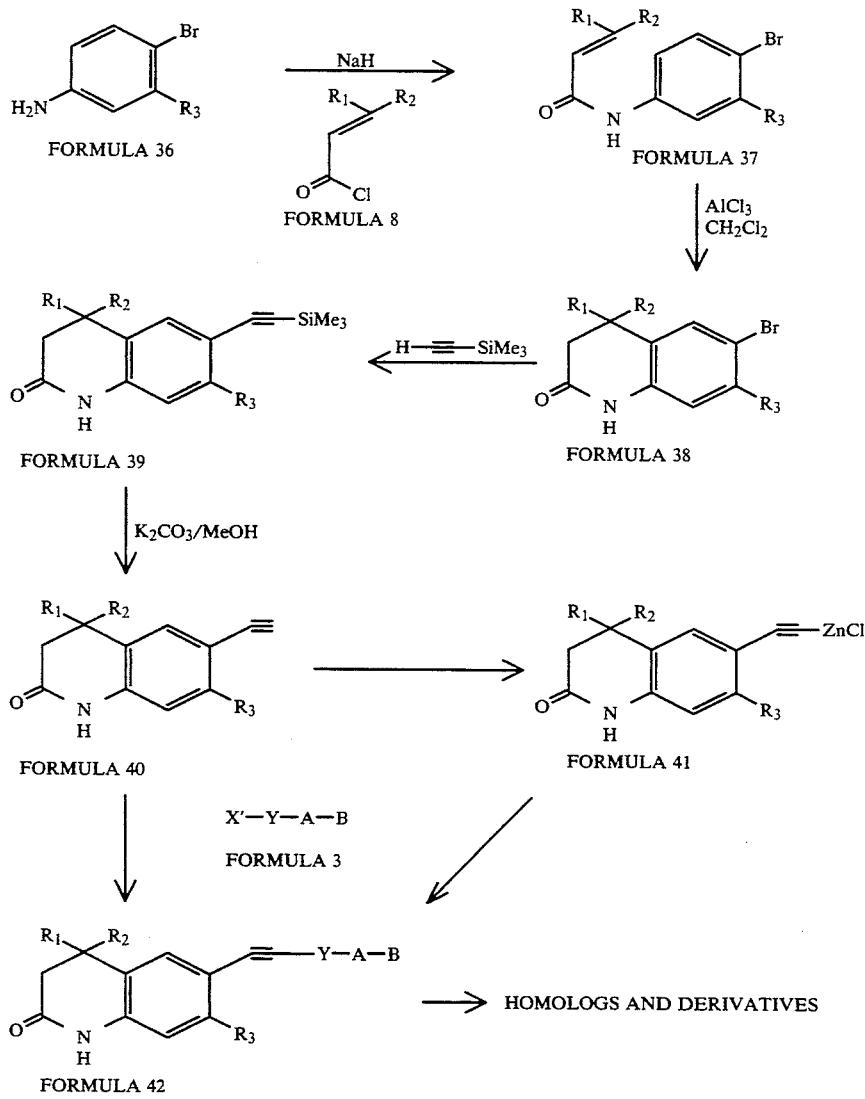
Reaction Scheme 6
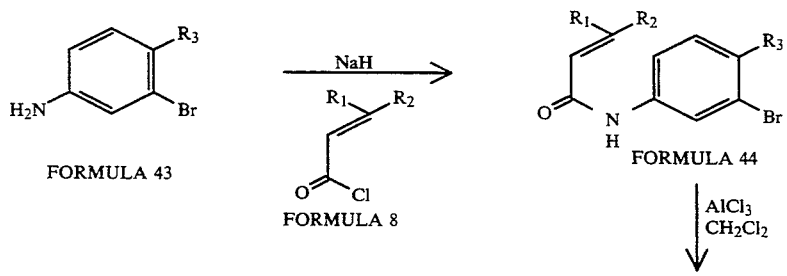

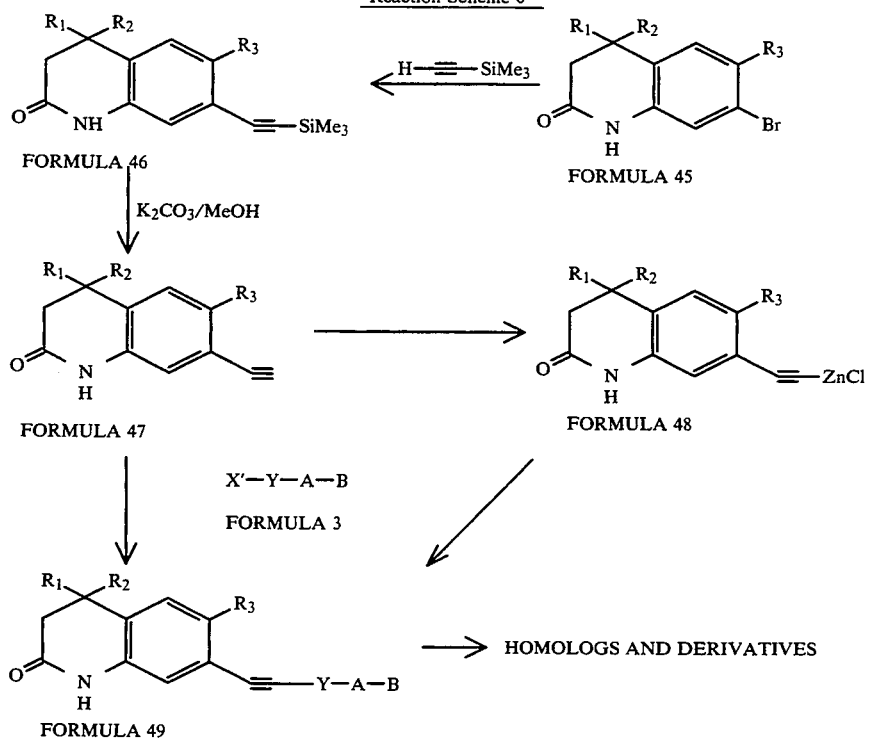

Reaction Schemes 5 and 6 illustrate examples of synthesis of the compounds of Formula 1 where X=NH. In Reaction Scheme 5 the ethynyl group is located in the 6 position of the lactame ring, and in Reaction Scheme 6 the ethynyl group is located in the 7 position of the lactame. The steps shown in Reaction Schemes 5 and 6 are analogous to the reaction steps in the preceding schemes, and are described here briefly.

Thus, with reference to Reaction Scheme 5, the 4-bromo-aniline, or a 4-bromo-aniline substituted in the 3-(meta) positions by an alkyl substituent ($R_3$) of Formula 36 is acylated with the acyl chloride of Formula 8. The resulting substituted amide (Formula 37) is ring closed under Friedel Crafts conditions to provide the 2-oxo-6-bromo-lactame of Formula 38. The acetylene portion is introduced into the substituted 2-oxo-6-bromo-lactame of Formula 37, using the same conditions as described above, to give the trimethylsilyl compound of Formula 39. The trimethylsilyl moiety is removed from the molecule of Formula 39 (as e.g. in Reaction Scheme 1) to provide the ring substituted 6-ethynyl-2-oxo-lactame (Formula 40). The 6-ethynyl-2-oxo-lactame (Formula 40), or alternatively the corresponding metal (zinc) salt (Formula 41), is subjected to substantially the same reaction procedures as described above (e.g. in Reaction Scheme 1) to yield the products of Formula 42.

Reaction Scheme 6 discloses substantially the same reaction steps as Reaction Scheme 5, except that the starting material is a 3-bromo-aniline (Formula 43) which may be alkyl substituted ($R_3$) in the 4 (para) position. The products of this reaction sequence are the 7-ethynyl substituted 1,2,3,4-tetrahydroquinoline derivatives of Formula 49.

Specific Examples (4-bromophenyl) 3,3-dimethylacrylate

To an ice bath cooled solution of 1.66 g (69.2 mmol) of NaH (60% suspension in mineral oil) in 25 ml of dry THF was added slowly under argon a solution of 10.0 g (57.8 mmol) of 4-bromophenol in 50 ml of dry THF. The mixture was stirred at 0 degrees C. for 30 minutes and then treated with a solution of 6.85 g (6.44 ml, 57.8 mmol) of dimethylacryloyl chloride in 25 ml of dry THF. The cooling bath was then removed and the mixture allowed to warm to room temperature. The organic layer was separated and the aqueous layer was washed with 2×25 ml of ether. The combined organic layers were washed with 2×50 ml of water, brine and dried ($MgSO_4$). The solvent was removed in-vacuo and the residue purified using flash chromatography ($SiO_2$; 5% ethyl acetate in hexanes) to give the title compound as a pale yellow oil.

PMR($CDCl_3$): 1.95(3H,d,J~1.5 Hz), 2.20(3H,d,J~1.4 Hz), 5.88(1H,m), 6.98(2H,d,J~8.9 Hz), 7.46(2H,d,J~8.9 Hz)

4,4-Dimethyl-6-bromo-2-oxo-chroman

To a stirred, ice cooled suspension of 11.5 g (86.3 mmol) of aluminum chloride in 200 ml of methylene chloride was added a solution of 11.0 g (43.1 mmol) of (4-bromophenyl) 3,3-dimethyl-acrylate in 100 ml of methylene chloride. The mixture was then stirred at room temperature for 20 hours and then poured into ice/brine mixture. The mixture was extracted with methylene chloride and the combined orgainc extracts were washed with water, brine and dried (MgSO4). The solvent was removed in-vacuo and the resulting residue purified using flash chromatography ($SiO_2$; 4% ethyl acetate in hexanes) to give the title compound as a yellow oil.

PMR($CDCl_3$): 1.37(6H,s), 2.64(2H,s), 6.96(1H,d,J~8.5 Hz), 7.38(1H,dd,J~8.5 Hz,J~2.3 Hz), 7.45(1H,d,J~2.3 Hz).

4,4-dimethyl-6-trimethylsilylethynyl-2-oxo-chroman

The procedure used is substantially in accordance with (Journal of Organic Chemistry, Vol. 46, No. 11, (1981) p 2280–81). To a solution of 2.5 g (9.8 mmol) of 4,4-dimethyl-6-bromo-2-oxo-chroman and 0.087 g (0.3317 mmol) of triphenylphosphine in 36 ml of triethylamine under argon was added 1.74 g (2.5 ml, 17.7 mmol) of trimethylsilylacetylene and 0.027 g (0.12 mmol) of palladium(II) acetate. The mixture was refluxed for 20 hours then cooled to room temperature and filtered. The solvent removed in-vacuo and the resulting residue was purified using flash chromatography (SiO$_2$; 5% ethyl acetate in hexanes) to give the title compound as a yellow oil.

PMR(CDCl$_3$): 0.227(9H,s), 1.32(6H,s), 2.56(2H,s), 6.95(1H,d,J∼8.3 Hz), 7.32(1H,dd,J∼8.3 Hz, J∼1.9 Hz), 7.39(1H,J∼1.9 Hz)

4,4-dimethyl-6-ethynyl-2-oxo-chroman

To a solution of 2.15 g (8.0 mmol) of 4,4-dimethyl-6-trimethylsilylethynyl-2-oxo-chroman in 25 ml of methanol was added, under nitrogen, 1.0 g of potassium carbonate. The reaction mixture was stirred at room temperature for 12 hours and the methanol was then removed under vacuum. The residue was extracted with methylene chloride (2×15 ml) and the combined organic layers were washed with dilute HCl, water, brine and dried (MgSO$_4$). The solvent was removed in-vacuo and the residue purified by Kugelrohr distillation to give the title compound as a yellow oil.

PMR(CDCl$_3$): 1.29(6H,s), 2.57(2H,s), 3.02(1H,s), 6.94(1H,d,J∼8.4 Hz), 7.32(1H,dd,J∼8.4 Hz,J∼1.95 Hz), 7.39 (1H,d,J∼1.95 Hz).

Ethyl 6-Chloronicotinate

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and residue subjected to flash chromatography to give the title compound as a low-melting white solid.

PMR (CDCl$_3$): 1.44 (3H, t, J∼6.2 Hz) 4.44 (2H, q, J∼4.4 Hz), 7.44 (1H, d, J∼8.1 Hz), 8.27 (1H, dd, J∼8.1 Hz, 3 Hz), 9.02 (1H, d, J∼3 Hz).

Ethyl 6-[4,4-dimethyl-2-oxo-chroman-6-yl] ethynylnicotinate (Compound 1)

To 0.305 g (1.5 mmol) of 4,4-dimethyl-6-ethynyl-2-oxo-chroman was added 0.278 g (1.5 mmol) of ethyl 6-chloronicotinate in 1 ml of triethylamine under bubbling nitrogen in a heavy walled glass tube, degassed under vacuum. Then mixture was then treated with a mixture of 30 mg of cuprous iodide and 60 mg of bis(triphenylphosphine) palladium (II) chloride, and the tube was again degassed under vacuum and flushed with nitrogen. The tube was sealed and the reaction mixture was heated at 60 degrees C. for 48 hours. The reaction mixture was cooled and taken up with methylene chloride and silica. Solvent was removed and the resulting residue was purified using flash chromatography (SiO$_2$; 1 L 10% ethyl acetate in hexanes, 1 L 12% ethyl acetate in hexanes, 2 L 15 % ethyl acetate in hexanes) to give the title compound as a pale yellow solid.

PMR (CDCl$_3$): 1.38–1.45(9H,m), 2.66(2H,s), 4.43(2H,q), 7.08(1H,d,J∼8.3 Hz), 7.52(1H,dd,J∼8.3 Hz, J∼1.9 Hz), 7.59–7.62(2H,m), 8.3(1H,dd,J∼8.25 Hz,J∼2.1 Hz), 9.22 (1H,d,J∼2.1 Hz).

Ethyl 4-iodobenzoate

To a suspension of 10 g (40.32 mmol) of 4-iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated NaHCO$_3$ and saturated NaCl solutions and dried (MgSO$_4$). Solvent was then removed in vacuo and the residue kugelrohr distilled (100 degrees C.; 0.55 mm) to give the title compound as a colorless oil, PMR (CDCl$_3$): 1.42 (3H, t, J∼7 Hz), 4,4 (2H, q, J∼7 Hz), 7.8 (4H).

Ethyl 4-[4,4-dimethyl-2-oxo-chroman-6-yl] ethynylbenzoate (Compound 2)

To 0.322 g (1.6 mmol) of 4,4-dimethyl-6-ethynyl-2-oxo-chroman was added 0.450 g (1.5 mmol) of ethyl 4-iodobenzoate in 1 ml of triethylamine under bubbling nitrogen in a heavy walled glass tube, degassed under vaccum. The mixture was then treated with a mixture of 30 mg of cuprous iodide and 60 mg of bis(triphenylphosphine) palladium (II) chloride and the tube was again degassed under vacuum and flushed with nitrogen. The tube was sealed and the reaction mixture was heated at 60 degrees C. for 48 hours. The reaction mixture was cooled and taken up with methylene chloride and silica. Solvent was removed and the resulting residue was purified using flash chromatography (SiO$_2$; 10% ethyl acetate in hexanes) to give the title compound as a white solid.

PMR (CDCl$_3$): 1.39–1.43(9H,m), 1.66(2H,s), 4.39(2H,q), 7.07(1H,d,J∼8.3 Hz), 7.45(1H,dd, J∼8.3 Hz,J∼1.9 Hz), 7.52(1H,d,J∼1.9 Hz), 7.60(1H,d,J∼8.4 Hz), 8.06(1H,d,J∼8.4 Hz)

4-[4,4-Dimethyl-2-oxo-chroman-6-yl]ethynyl]benzoic acid (Compound 2a)

To a solutiion of 0.21 g (0.6 mmol) of ethyl 4-[4,4-dimethyl-2-oxo-chroman-6-yl]ethynyl]benzoate in 10 ml of anhydrous THF was added 10 ml of 0.5N lithium hydroxide solution. The reagents were stirred together at ambient temperature until the reaction was complete, as monitored by TLC. The reaction mixture was concentrated in vacuo, diluted with water and washed with diethyl ether. The aqueous phase was diluted with diethyl ether, acidified with conc. HCl (pH∼1) and the layers were separated. The aqueous phase was washed three times with ether and then all organic phases were combined, washed with brine solution, dried over Na$_2$SO$_4$, filtered and concentrated in vacuo to give the title compound as an off-white solid.

PMR (DMSO-d$_6$): δ1.31 (6H, s), 2.78(2H, s), 7.16(1H, d, J=8.4 Hz), 7.54(1H, dd, J=8.4, 2 Hz), 7.66(1H, d, J=2 Hz), 7.68(2H, J=8.1 Hz), 7.98(2H, J=8.1 Hz).

S-(4-bromophenyl) 3,3-dimethylthioacrylate

To an ice bath cooled solution of 1.92 g (80 mmol) of NaH (obtained from a 60% suspension in mineral oil by 3×15 ml hexane wash) in 30 ml of dry THF was added slowly under argon a solution of 15.1 g (80 mmol) of 4-bromothiophenol in 60 ml of dry THF over 1 hour. The mixture was stirred at 0 degrees C. for a further 30 min and then treated with a solution of 10.1 g (85 mmol) of dimethylacryloyl chloride in 30 ml of dry THF. The cooling bath was then removed and the mixture then stirred at room temperature for 40 h. The reaction mixture was poured into 200 ml of water containing 2 ml of glacial acetic acid and the organic layer was separated. The organic layer was washed with 2×75 ml of water and then dried (MgSO$_4$). The solvent was removed in vacuo to give the title compound as a yellow oil.

PMR (CDCl$_3$): 1.91 (3H, s), 2.14 (3H, s), 6.03–6.06 (1H, m), 7.28 (2H, d, J∼8.6 Hz), 7.53 (2H, d, J∼8.6 Hz).

4,4-Dimethyl-6-bromo-2-oxo-thiochroman

To a stirred, ice-cooled suspension of 15.9 g (119 mmol) of aluminum chloride in 140 ml of methylene chloride was added under nitrogen a solution of 21.64 g (79.9 mmol) of S-(4-bromophenyl) 3,3-dimethylthioacrylate in 100 ml of methylene chloride. The mixture was then stirred at room temperature for 72 h and then poured into 250 g of an ice and brine mixture. The mixture was extracted with methylene chloride and the combined organic extracts were washed with saturated NaCl solution and then dried (MgSO$_4$). The solvent was removed in vacuo and the residue recrystallized from hexanes to give the title compound as white crystals.

PMR (CDCl$_3$): 1.40 (6H, s), 2.67 (2H, s), 7.31–7.40 (3H, m). MS exact mass, m/e 269.9714 (calcd. for C$_{11}$H$_{11}$SOBr, 269.9714).

4,4-Dimethyl-6-trimethylsilylethynyl-2-oxo-thiochroman

A solution of 1.0 g (3.7 mmol) of 4,4-dimethyl-6-bromo-2-oxo-thiochroman in 1 ml of triethylamine was placed in a heavy-walled tube and degassed and then treated under argon with 2.0 g (2.75 ml, 20.0 mmol) of trimethylsilylacetylene and a powdered mixture of 0.038 g of cuprous iodide and 0.084 g of bis(triphenylphosphine) palladium (II) chloride. The reaction mixture was degassed again, then placed under argon and the tube was sealed. The mixture was heated at 55 degrees C. for 24 hours, allowed to cool to room temperature and taken up with methylene chloride and silica. Solvent was removed in-vacuo and the resulting residual material on silica was purified using flash chromatography (SiO$_2$; 2% ethyl acetate in hexanes) to give the title compound as a yellow oil.

PMR(CDCl$_3$): 0.218(9H,s), 1.34(6H,s), 2.56(2H,s), 7.22(1H,d,J~2 Hz), 7.25(1H,dd,J~8.1 Hz,J~2.0 Hz), 7.33(1H,d,J~8.1 Hz.

S-(3-Bromophenyl) 3,3-dimethyl-thio acrylate

To an ice-bath cooled solution of 4.5 g (112.5 mmol) of sodium hydride (60% suspension in mineral oil) in 50 ml of dry THF was added slowly under argon a solution of 20 g (105.8 mmol) of 3-bromothiophenol in 80 ml of dry THF. The mixture was stirred at 0° C. for 30 minutes and then treated with a solution of 14 g (118 mmol) of dimethylacryloyl chloride in 30 ml of dry THF. The reaction mixture was allowed to stir at room temperature for 24 hours. The reaction mixture was poured onto 300 ml of water containing 5 ml of glacial acetic acid and the organic layer was separated. The aqueous layer was extracted with 2×200 ml ether. The organic extracts were combined and washed with 100 ml of water and 100 ml of saturated NaCl solution and then dried (MgSO$_4$). The solvent was removed in vacuo and the residue was kugelrohr distilled to give the title compound as a pale yellow oil.

PMR (CDCl$_3$); 1.90 (3H, s), 2.14 (3H, s), 6.04 (1H, s), 7.26 (1H, t, J~7.8 Hz), 7.36 (1H, d, J~4 Hz), 7.5 (1H, dd, J~7.8 Hz, J~1.7 Hz), 7.59 (1H, d, J~1.7 Hz)

4,4 Dimethyl-7-bromo-2-oxo-thiochroman

To a stirred, ice cooled suspension of 20 g (150 mmol) of aluminum chloride in 250 ml of methylene chloride was added a solution of 17 g (89.5 mmol) of S-(3-bromophenyl) 3—3 dimethyl-thio acrylate in 100 ml of methylene chloride. The mixture was stirred at room temperature for 24 hours and then poured into 200 ml of an ice and brine mixture. The organic layer was separated and the aqueous layer was extracted with 150 ml of ether. The organic extracts were combined and then washed with water and saturated NaCl solution and dried (MgSO$_4$). The solvent was removed in vacuo and the residue purified by flash column chromatography (silica; 2% ethyl acetate, hexanes) to give the title compound as a white solid.

PMR (CDCl$_3$); 1.38 (6H, s), 2.65 (2H, s) 7.33 (3H, s).

4,4-dimethyl-7-trimethylsilylethynyl-2-oxo-thiochroman

A solution of 1.0 g (3.7 mmol) of 4,4-dimethyl-7-bromo-2-oxo-thiochroman in 1 ml of triethylamine was placed in a heavy-walled tube and degassed and then treated under argon with 2.0 g (2.75 ml, 20.0 mmol) of trimethylsilylacetylene and a powdered mixture of 0.038 g of cuprous iodide and 0.084 g of bis(triphenylphosphine) palladium (II) chloride. The reaction mixture was degassed again, then placed under argon and the tube was sealed. The mixture was heated at 55 degrees C. for 24 hours, and thereafter allowed to cool to room temperature. Solvent was removed in-vacuo to give the title compound as a yellow oil.

PMR(CDCl$_3$): 0.05(9H,s), 1.40(6H,s), 1.69(2H,s), 7.26–7.42(3H,m).

3-Bromophenyl 3,3-dimethyl acrylate

To an ice-cooled suspension of 4 g (100 mmol) of sodium hydride (60% in mineral oil) in 50 ml of dry THF was added dropwise a solution of 15.7 g(90.7 mmol) of 3-bromo phenol in 25 ml of dry THF. The mixture was stirred at 0 degrees C. for 0.5 hours and then treated with a solution of 10.65 g (90.0 mmol) of dimethyl acryloyl chloride in 30 ml of dry THF. The mixture was allowed to warm to room temperature and stirred for 24 hours. The reaction mixture was poured onto 200 ml of ice water containing 3 ml of glacial acetic acid. The mixture was extracted with 2×250 ml ether and the combined ether extracts were washed with 200 ml of water and 100 ml saturated NaCl solution and dried (MgSO$_4$). The solvent was removed in vacuo and the residue purified by kugelrohr distillation to give the title compound as a clear oil.

PMR (CDCl$_3$): 2.02 (3H, s), 2.28 (3H, s), 5.94 (1H, broad s), 7.06–7.12 (1H, m ), 7.28 (1H, t, J~8.0 Hz), 7.34 (1H, t, J~2.0 Hz), 7.37–7.42 (1H, m).

4,4-dimethyl-7-bromo-2-oxochroman

To a stirred, ice-cooled suspension of 21 g (158 mmol) of aluminum chloride in 200 ml of methylene chloride was added slowly a solution of 23.74 g (93.1 mmol) of 3-bromo-phenyl-3,3-dimethyl acrylate in 100 ml of methylene chloride. The mixture was warmed to room temperature and stirred for 52 hours. The mixture was poured into a mixture of ice and brine and the organic layer was separated. The aqueous layer was extracted with 2×100 ml ether. The organic extracts were combined and washed with 2×250 ml of water and 50 ml of saturated NaCl solution and dried (MgSO$_4$). The solvent was removed in vacuo and the residue was partially purified by flash column chromatography, (silica; 5% ethyl acetate/hexane) to give the title compound as an impure yellow oil.

4,4-dimethyl-6-bromo-2-oxo-quinoline

To a solution of 10.0 g (84 mmol) of dimethylacryloyl chloride in 200 ml of dry THF was added a solution of 4-bromo aniline in 250 ml of dry THF. The mixture was stirred at room temperature for 2 hours and extracted with hexane. The combined organic extracts were washed with water, brine and dried (MgSO$_4$). Solvent was removed in-vacuo and the residue was partially purified by recrystallization (20% ethyl acetate in hexanes) to give (4-bromophenyl) 3,3-dimethylacryloylamide as white crystals which was used in the next step without further purification.

To 1.0 g (3.9 mmol) of (4-bromophenyl) 3,3-dimethylacryloylamide heated to 130 degrees C. was added 0.526 g (3.94 mmol) of aluminum chloride over a period of 30 minutes. The reaction mixture was heated for an additional 30 minutes. The mixture was treated again with 0.079 g (0.592 mmol) of aluminum chloride and heated at 130 degrees C. for 1 hour and 40 minutes. The reaction mixture was extracted with 20 ml ether and the combined organics washed with 20 ml water, 20 ml brine and dried (MgSO4). Solvent was removed invacuo and the residue purified by flash chromatography (SiO2; 20% ethyl acetate in hexanes) to give the title compound as a light yellow solid.

PMR(CDCl3): 1.37(6H,s), 2.52(2H,s), 6.85(1H,d,J~8.2 Hz), 7.32(1H,dd,J~8.2 Hz, J~2.1 Hz), 7.43(1H,J~2.1 Hz), 10.2 (1H, s).

What is claimed is:

1. A compound of the formula

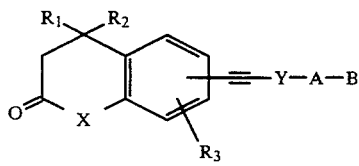

where $R_1$ and independently $R_2$ are hydrogen, lower alkyl of 1–6 carbons, or halogen;

$R_3$ is hydrogen, lower alkyl of 1–6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$;

X is O, S or NR' where R' is hydrogen or lower alkyl of 1–6 carbons;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

2. A compound of claim 1 where X is O.

3. A compound of claim 2 where A is $(CH_2)_n$ and n is 0, 1 or 2.

4. A compound of the formula

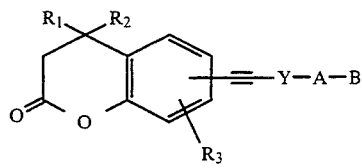

where $R_1$ and $R_2$ are hydrogen, lower alkyl of 1–6 carbons, or halogen;

$R_3$ is hydrogen, lower alkyl of 1–6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0, 1, or 2, and

B is COOH or a pharmaceutically acceptable salt, thereof, or B is $COOR_8$ or $COONR_9R_{10}$ where $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl.

5. A compound of the formula

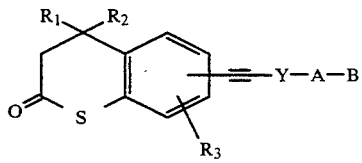

where $R_1$ and $R_2$ are hydrogen, lower alkyl of 1–6 carbons, or halogen;

$R_3$ is hydrogen, lower alkyl of 1–6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$, is lower alkyl, and $R_{13}$ is divalent alkyl radical of 2–5 carbons.

6. A compound of claim 5 where A is $(CH_2)_n$ and n is 0, 1 or 2.

7. A compound of claim 6 where B is COOH or a pharmaceutically acceptable salt, thereof, or B is COOR$_8$ or COONR$_9$R$_{10}$.

8. A compound of claim 1 where X is NR'.

9. A compound of claim 8 where A is (CH$_2$)$_n$ and n is 0, 1 or 2.

10. A compound of the formula

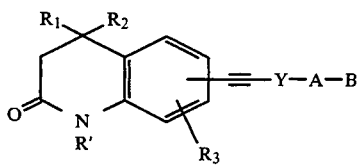

where R$_1$ and R$_2$ are hydrogen, lower alkyl of 1–6 carbons, or halogen;

R$_3$ is hydrogen, lower alkyl of 1–6 carbons, halogen, OR$_{11}$, SR$_{11}$, OCOR$_{11}$, SCOR$_{11}$, NH$_2$, NHR$_{11}$, N(R$_{11}$)$_2$, NHCOR$_{11}$ or NR$_{11}$COR$_{11}$;

R' is hydrogen or lower alkyl of 1–6 carbons;

Y is phenyl or a heteroaryl group selected from a group consisting of pyridyl, thienyl, furyl, pyridazinyl, pyrimidinyl, pyrazinyl, thiazolyl and oxazolyl;

A is (CH$_2$)$_n$ where n is 0, 1, or 2, and

B is COOH or a pharmaceutically acceptable salt, thereof, or B is COOR$_8$ or COONR$_9$R$_{10}$ where R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl.

11. A compound of the formula

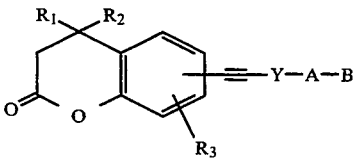

where R$_1$ and R$_2$ independently are hydrogen, lower alkyl of 1–6 carbons, or halogen;

R$_3$ is hydrogen, lower alkyl of 1–6 carbons, or halogen;

Y is phenyl or a heteroaryl group selected from a group consisting of pyridyl, thienyl, furyl, pyridazinyl, pyrimidinyl, pyrazinyl, thiazolyl and oxazolyl;

A is (CH$_2$)$_n$ where n is 0–5, lower branched chain alkyl having 3–6 carbons, or cycloalkyl having 3–6 carbons;

B is COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

12. A compound of claim 11 where Y is phenyl.

13. A compound of claim 12 where A is (CH$_2$)$_n$ and n is 0.

14. A compound of claim 13 where the ethynyl group is in the 6 position of the chroman ring.

15. A compound of the formula

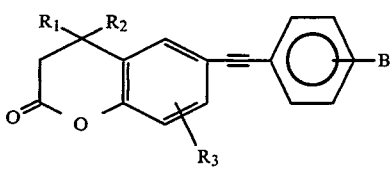

where R$_1$ and R$_2$ are methyl, and R$_3$ is H;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons.

16. A compound of claim 15 where the ethynyl and B groups are in 1,4 positions of the phenyl ring.

17. The compound of claim 16 where B is COOC$_2$H$_5$.

18. The compound of claim 16 where B is COOH, or a pharmaceutically acceptable salt thereof.

19. A compound of the formula

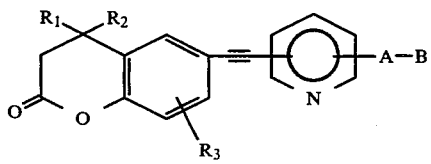

where

R$_1$ and R$_2$ are hydrogen, lower alkyl of 1–6 carbons, or halogen;

R$_3$ is hydrogen, lower alkyl of 1–6 carbons, or halogen;

A is (CH$_2$)$_n$ where n is 0–5, lower branched chain alkyl having 3–6 carbons, or cycloalkyl having 3–6 carbons;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, or CR$_7$OR$_{13}$O, where R$_7$ is an alkyl, cycloalkyl or alkenyl group containing 1 to 5 carbons, R$_8$ is an alkyl group of 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and $R_{13}$ is divalent alkyl radical of 2-5 carbons.

20. A compound of claim 19 where A is $(CH_2)_n$ and n is 0.

21. A compound of claim 20 where the ethynyl group is in the 6 position of the chroman ring.

22. A compound of claim 21 where $R_1$ and $R_2$ are methyl, and $R_3$ is H.

23. A compound of claim 22 where the ethynyl and A-B groups are in 2,5 positions of the pyridine ring.

24. The compound of claim 23 where B is $COOC_2H_5$.

25. A compound of the formula

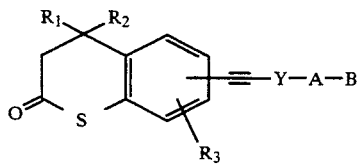

where $R_1$ and $R_2$ are hydrogen, lower alkyl of 1-6 carbons, or halogen;

$R_3$ is hydrogen, lower alkyl of 1-6 carbons, or halogen;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0-5, lower branched chain alkyl having 3-6 carbons, or cycloalkyl having 3-6 carbons;

B is hydrogen, COOH of a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower/alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is Lower alkyl, and $R_{13}$ is divalent alkyl radical of 2-5 carbons.

26. A compound of claim 25 where the Y group is phenyl.

27. A compound of claim 25 where the Y group is selected from a group consisting of pyridyl, thienyl and furyl.

28. A compound of the formula

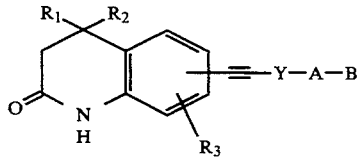

where $R_1$ and $R_2$ are hydrogen, lower alkyl of 1-6 carbons, or halogen;

$R_3$ is hydrogen, lower alkyl of 1-6 carbons, or halogen;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0-5, lower branched chain alkyl having 3-6 carbons, or cycloalkyl having 3-6 carbons;

B is COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

29. A compound of the formula

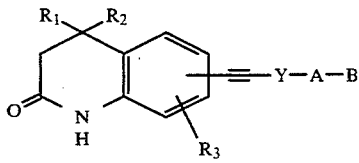

where

Y is phenyl;

$R_1$ and $R_2$ are hydrogen, lower alkyl of 1-6 carbons, or halogen;

$R_3$ is hydrogen, lower alkyl of 1-6 carbons, or halogen;

A is $(CH_2)_n$ where n is 0-5, lower branched chain alkyl having 3-6 carbons, or cycloalkyl having 3-6 carbons;

B is hydrogen, COOH or a pharmaceutically acceptable salt thereof, $COOR_8$, $CONR_9R_{10}$, $-CH_2OH$, $CH_2OR_{11}$, $CH_2OCOR_{11}$, CHO, $CH(OR_{12})_2$, $CHOR_{13}O$, $-COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5-10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2-5 carbons.

30. A compound of claim 28 where the Y group is selected from a group consisting of pyridyl, thienyl and furyl.

31. A pharmaceutical composition comprising a pharmaceutically acceptable excipient and one or more compounds set forth in claim 1 as the active ingredient.

32. A method for treating skin disorders in a mammal which method comprises administering alone or in conjunction with a pharmaceutically acceptable excipient a therapeutically effective amount of one or more compounds of the formula

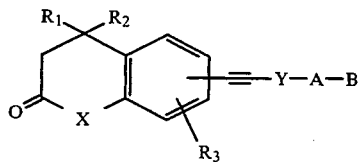

where $R_1$ and $R_2$ are hydrogen, lower alkyl of 1–6 carbons, or halogen;

$R_3$ is hydrogen, lower alkyl of 1–6 carbons, halogen, $OR_{11}$, $SR_{11}$, $OCOR_{11}$, $SCOR_{11}$, $NH_2$, $NHR_{11}$, $N(R_{11})_2$, $NHCOR_{11}$ or $NR_{11}COR_{11}$;

X is O, S or NR' where R' is hydrogen or lower alkyl of 1–6 carbons;

Y is phenyl or a heteroaryl group selected from a group consisting of pyridyl, thienyl, furyl, pyridazinyl, pyrimidinyl, pyrazinyl, thiazolyl and oxazolyl;

A is $(CH_2)_n$ where n is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, $COOR_8$, $CONR_9R_{10}$, $—CH_2OH$, $CH_2OR_{11}$, $CH_2OCOR_{11}$, CHO, $CH(OR_{12})_2$, $CHOR_{13}O$, $—COR_7$, $CR_7(OR_{12})_2$, or $CR_7OR_{13}O$, where $R_7$ is an alkyl, cycloalkyl or alkenyl group containing 1 to 5 carbons, $R_8$ is an alkyl group of 1 to 10 carbons, or a cycloalkyl group of 5 to 10 carbons, or $R_8$ is phenyl or lower alkylphenyl, $R_9$ and $R_{10}$ independently are hydrogen, an alkyl group of 1 to 10 carbons, or a cycloalkyl group of 5–10 carbons, or phenyl or lower alkylphenyl, $R_{11}$ is lower alkyl, phenyl or lower alkylphenyl, $R_{12}$ is lower alkyl, and $R_{13}$ is divalent alkyl radical of 2–5 carbons.

* * * * *

UNITED STATES PATENT AND TRADEMARK OFFICE
CERTIFICATE OF CORRECTION

PATENT NO. : 5,399,561
DATED : March 21, 1995
INVENTOR(S) : Roshantha A. Chandraratna It is certified that error appears in the above-identified patent and that said Letters Patent is hereby corrected as shown below:

Column 2, line 15, "substitited" should be --substituted--;

Column 2, line 23-25, "disubsituted" should be --disubstituted--;

Column 4, line 9, "$(CH2)_n$" should be --$(CH_2)_n$--;

Column 12, line 59, "by by" should be --by--.

UNITED STATES PATENT AND TRADEMARK OFFICE
CERTIFICATE OF CORRECTION

PATENT NO. : 5,399,561

DATED : March 21, 1995

INVENTOR(S) : Roshantha A. Chandraratna

It is certified that error appears in the above-identified patent and that said Letters Patent is hereby corrected as shown below:

Column 10, line 45, "trimethylsityl" should be --trimethylsilyl--;

Column 20, line 60, "MgSO4" should be --$MgSO_4$--;

Column 29, line 39, after "lower" please delete "/".

Signed and Sealed this

Twenty-sixth Day of December, 1995

Attest:

BRUCE LEHMAN

Attesting Officer     Commissioner of Patents and Trademarks